US00PP23251P2

(12) United States Plant Patent
Egger

(10) Patent No.: US PP23,251 P2
(45) Date of Patent: Dec. 11, 2012

(54) ***TRADESCANTIA* PLANT NAMED 'REGAL CHARM'**

(50) Latin Name: ***Tradescantia Andersoniana* Group**
Varietal Denomination: Regal Charm

(75) Inventor: Janet N. Egger, Wilsonville, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 0 days.

(21) Appl. No.: 13/200,459

(22) Filed: Sep. 22, 2011

(51) Int. Cl.
*A01H 5/00* (2006.01)

(52) U.S. Cl. ..... Plt./263.1

(58) Field of Classification Search ..... Plt./263.1
See application file for complete search history.

*Primary Examiner* — Annette Para

(74) *Attorney, Agent, or Firm* — Klarquist Sparkman, LLP

(57) ABSTRACT

A new and distinct cultivar of *Tradescantia* plant characterized by yellow gold to yellow green foliage, deep violet flowers, a compact clumping habit, and excellent vigor.

1 Drawing Sheet

Botanical denomination: *Tradescantia Andersoniana* Group.

Variety designation: 'Regal Charm'.

BACKGROUND OF THE INVENTION

The present invention relates to a new and distinct cultivar of *Tradescantia*, given the name, 'Regal Charm'. *Tradescantia* is in the family Commelinaceae. This new variety is from a planned breeding cross for yellow foliage, compact *Tradescantia*. The new cultivar is a seedling from the cross of *Tradescantia* 'Sunshine Charm' (U.S. Plant Pat. No. 21,480), as the seed parent and *Tradescantia* 28-2 a proprietary, unnamed seedling, as the pollen parent. Compared to the seed parent, *Tradescantia* 'Sunshine Charm', the new cultivar has deep violet rather than dark pink flowers. Compared to the pollen parent, *Tradescantia* 28-2, the new cultivar has yellow gold to yellow green foliage rather than green foliage. Compared to *Tradescantia* 'Blue and Gold' (syn. 'Sweet Kate') (unpatented), the new cultivar has a more compact habit and deep violet rather than blue flowers.

SUMMARY OF THE INVENTION

This plant exhibits the following characteristics that make it unique:

1. a compact clumping habit,
2. yellow gold to yellow green foliage,
3. deep violet flowers, and
4. excellent vigor.

The new variety has been reproduced only by asexual propagation (cuttings and micropropagation). Each of the progeny exhibits identical characteristics to the original plant. Asexual propagation by division and micropropagation as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWING

FIG. 1 shows a two-year-old *Tradescantia* 'Regal Charm' growing in the garden in part shade late spring in Canby, Oreg.

DETAILED PLANT DESCRIPTION

The following is a detailed description of the new *Tradescantia* cultivar based on observations of two-year-old specimens grown outside in part shade in the garden in Canby, Oreg. Canby is Zone 8 on the USDA Hardiness map. Temperatures range from a high of 95 degrees F. in August to an average of 32 degrees F. in January. Normal rainfall in Canby is 42.8 inches per year. The color descriptions are all based on The Royal Horticultural Society Colour Chart, $5^{th}$ edition.

Plant:

*Form*.—Upright clumping.
*Type*.—Herbaceous perennial.
*Cold hardiness*.—USDA Zone 4-9.
*Size*.—Grows to 55 cm wide and 28 cm tall to the top of the foliage and flowers.
*Vigor*.—Excellent.
*Stem*.—Flowering, oval in cross section, swollen at nodes and leafy, grows to 8 mm wide and 19 cm tall to the last leaf, glabrous, internodes range from 3 to 11 cm long, Yellow Green 145B at mid stem and streaked to strongly tinted Greyed Purple N186C at base.
*Roots*.—Thick and fleshy, plants root easily from nodes or crown division.

Leaf:

*Type*.—Simple.
*Arrangement*.—Alternate.
*Shape*.—Linear-lanceolate.
*Venation*.—Parallel.
*Leaf description*.—Grows to 41 cm long and 17 mm wide, pleated at midrib toward the base, margin entire, tip acuminate, base sheathing, glabrous inside and out except near base where villous on margin.
*Leaf color*.—Varies with light, top and bottom side, ranges from Yellow 13B on top half and on margins to base, midrib to center base Yellow Green 144C, veins on sheaths Greyed Purple N186C.

Inflorescence:

*Type*.—Terminal umbel-like cyme subtended by 1 or 2 leafy bracts (smaller than the leaves, otherwise the similar, grow to 32 cm long, 18 mm wide, linear lanceolate, top and bottom side Yellow 13B to Yellow Green 144C at the base).

*Number of flowers per cyme*.—Up to 30.

*Size of inflorescence*.—5.5 cm tall and 6.5 cm wide.

*Peduncle*.—6.5 cm long and 4 mm wide, glabrous, Yellow 13C in sun and Yellow Green 151B in shade.

*Pedicel*.—20 mm long and 1.2 mm wide, glabrous, flattened, Purple N77B.

*Bloom period*.—Late May through July in Canby, Oreg.

Flower bud:

*Size*.—12 mm long and 7 mm wide at the widest point prior to opening.

*Description*.—Ovoid.

*Surface texture*.—Pubescent.

*Color*.—Yellow Green 145A.

Flower:

*Type*.—Actinomorphic to irregular, single.

*Size*.—38 mm wide and 12 mm deep.

*Corolla description*.—3 petals, each broadly ovate in shape, each 18 mm wide and 20 mm long, margins entire on sides with top ⅓ sometimes with notches, tip variable from acute to obtuse to notched, base obtuse, glabrous on both sides, top side Violet N87A except center base where N87B, bottom side Violet N87C to Violet N87A on edges.

*Calyx description*.—3 sepals, 10 mm long and 6 mm wide, pubescent outside and glabrous inside, ovate, cupped, entire, acute, Yellow Green 144A inside and out, margins Greyed Purple 187B.

*Pistil description*.—1 in number, 11 mm long, ovary 2 mm long, Yellow Green 145D, style 6 mm long, Violet 86A; stigma White NN155A.

*Stamen description*.—6 in number, 10 mm long, filaments 8 mm long and to 6 mm wide with long hairs, filaments and hairs Violet 86A, anthers reniform in shape, 1 mm long, Yellow 13A, pollen Yellow 13B.

*Fragrance*.—None.

*Lastingness*.—A cyme blooms for about 4 weeks on the plant, a flower lasts about a day.

Fruit/seed: Fruit a 3-valved, 3-loculed capsule, low fertility, seeds oval, 3 mm long and 2 mm wide, Brown N200A.

Pests and diseases: *Tradescantia Andersoniana* Group is known to be susceptible viruses, aphids, and spider mites. The new cultivar has no known resistances but has shown no problems in Canby, Oreg.

I claim:

1. A new and distinct *Tradescantia* plant as shown and described herein.

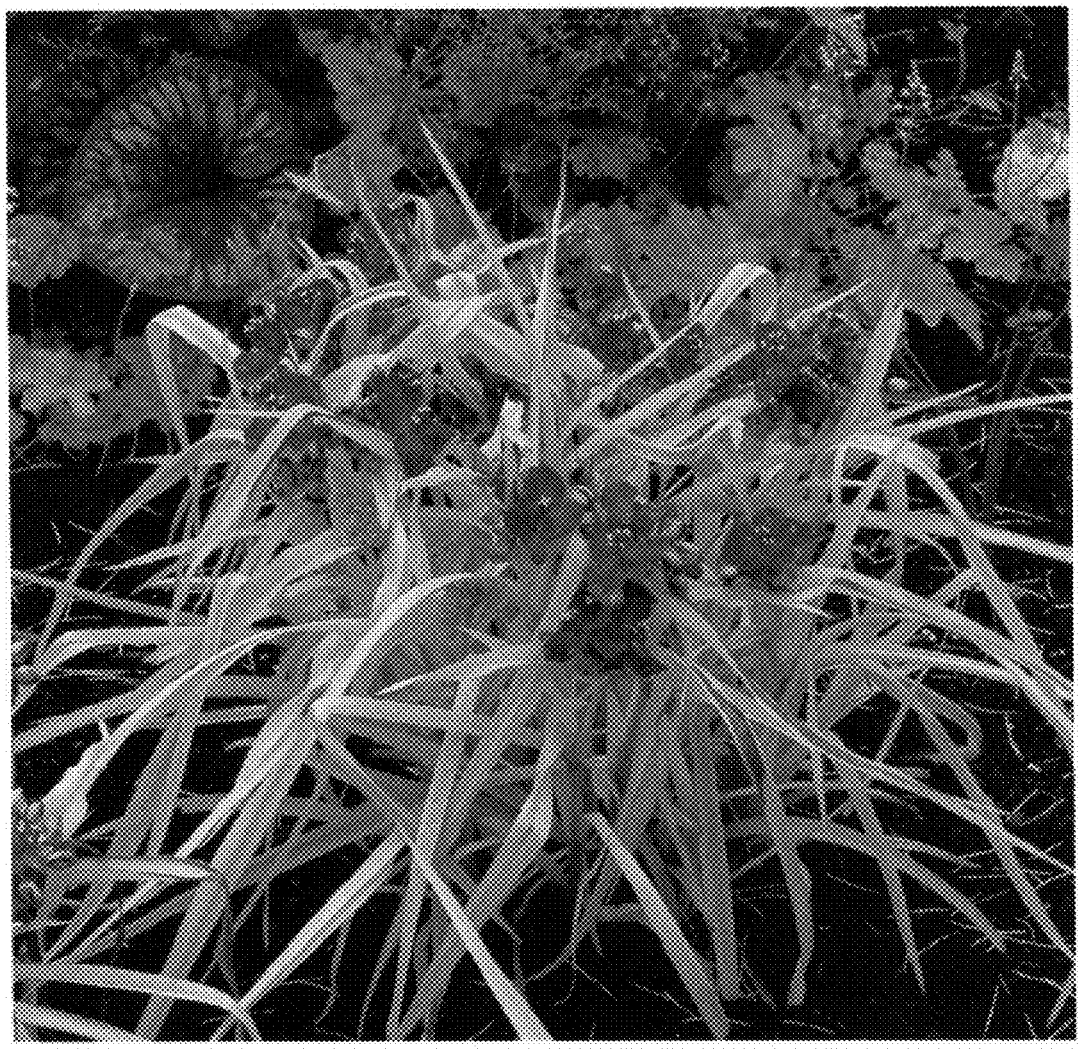

* * * * *